United States Patent
Bartolomé-Nebreda et al.

(10) Patent No.: US 8,530,474 B2
(45) Date of Patent: Sep. 10, 2013

(54) SUBSTITUTED 6-(1-PIPERAZINYL)-PYRIDAZINES AS 5-HT$_6$ RECEPTOR ANTAGONISTS

(75) Inventors: José Manuel Bartolomé-Nebreda, Toledo (ES); Gregor James MacDonald, Zoersel (BE); Michiel Luc Maria Van Gool, Madrid (ES); Susana Conde-Ceide, Toledo (ES); Francisca Delgado-Jiménez, Madrid (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/002,413

(22) PCT Filed: Jul. 1, 2009

(86) PCT No.: PCT/EP2009/004745
§ 371 (c)(1),
(2), (4) Date: Jan. 3, 2011

(87) PCT Pub. No.: WO2010/000456
PCT Pub. Date: Jan. 7, 2010

(65) Prior Publication Data
US 2011/0112107 A1    May 12, 2011

(30) Foreign Application Priority Data
Jul. 3, 2008  (EP) .................................... 08159591

(51) Int. Cl.
*A61K 31/50*  (2006.01)
*A61K 31/501* (2006.01)

(52) U.S. Cl.
USPC ..................................... 514/252.02; 544/238

(58) Field of Classification Search
USPC ..................................... 544/238; 514/252.02
See application file for complete search history.

(56) References Cited

U.S. PATENT DOCUMENTS

| | | | |
|---|---|---|---|
| 3,933,832 A | 1/1976 | Langbein et al. | |
| 4,126,689 A | 11/1978 | Sanczuk et al. | |
| 4,197,304 A | 4/1980 | Hermans et al. | |
| 4,585,471 A | 4/1986 | Forster et al. | |
| 5,736,545 A | 4/1998 | Gadwood et al. | |
| 5,866,589 A | 2/1999 | Romero et al. | |
| 7,754,774 B2 | 7/2010 | Kobayashi et al. | |
| 8,058,243 B2 | 11/2011 | Tyers et al. | |
| 2008/0227791 A1 | 9/2008 | Debruyn et al. | |
| 2010/0063058 A1 | 3/2010 | MacDonald et al. | |
| 2010/0069394 A1* | 3/2010 | MacDonald et al. | 514/252.02 |
| 2010/0076187 A1 | 3/2010 | MacDonald et al. | |
| 2010/0120860 A1 | 5/2010 | MacDonald et al. | |
| 2010/0137368 A1 | 6/2010 | MacDonald et al. | |
| 2010/0210687 A1 | 8/2010 | Cooper et al. | |
| 2011/0130408 A1 | 6/2011 | Bartolm-Nebreda et al. | |

FOREIGN PATENT DOCUMENTS

| | | |
|---|---|---|
| DE | 2642856 | 3/1977 |
| DE | 3218482 | 11/1983 |
| EP | 281309 | 9/1988 |
| EP | 532178 | 3/1993 |
| EP | 1443046 | 8/2004 |
| EP | 1621538 | 2/2006 |
| EP | 1506185 | 5/2006 |
| WO | WO 96/18628 | 6/1996 |
| WO | WO 96/35666 | 11/1996 |
| WO | WO 99/09025 | 2/1999 |
| WO | WO 99/36407 | 7/1999 |
| WO | WO 01/98273 | 12/2001 |
| WO | WO 02/068409 | 9/2002 |
| WO | WO 03/049736 | 6/2003 |
| WO | WO 03/062215 | 7/2003 |
| WO | WO 03/066604 | 8/2003 |
| WO | WO 03/072548 | 9/2003 |
| WO | WO 2005/005779 | 1/2005 |
| WO | 2005/009976 | 2/2005 |
| WO | WO 2005/013907 | 11/2005 |
| WO | WO 2005/105779 | 11/2005 |
| WO | WO 2005/117883 | 12/2005 |
| WO | WO 2006/034440 | 3/2006 |
| WO | WO 2006/055187 | 5/2006 |

(Continued)

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
International Search Report for PCT/EP2009/004745 dated Aug. 28, 2009.
Written Opinion for PCT/EP2009/004745 dated Aug. 28, 2009.
Abbott, A., Nature, vol. 447, May 24, 2007, p. 368-370.
Arlt, M. et al., Bioorganic & Medicinal Chemistry Letters; vol. 8; No. 15; p. 2033-2038, 1998.

(Continued)

*Primary Examiner* — James O Wilson
*Assistant Examiner* — Alexander R Pagano
(74) *Attorney, Agent, or Firm* — Hal B. Woodrow

(57) ABSTRACT

The present invention is concerned with novel substituted 6-(1-piperazinyl)-pyridazines of Formula (I)

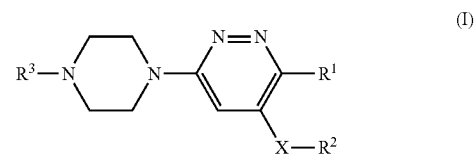

(I)

wherein $R^1$, $R^2$, $R^3$ and X have the meaning defined in the claims, having 5-HT$_6$-antagonistic properties. The invention further relates to processes for preparing such novel compounds, pharmaceutical compositions comprising said novel compound as an active ingredient as well as the use of said compounds as a medicine.

10 Claims, No Drawings

(56) References Cited

FOREIGN PATENT DOCUMENTS

| WO | WO 2007/001975 | | 1/2007 |
|---|---|---|---|
| WO | WO 2007/048779 | | 5/2007 |
| WO | WO 2007/130383 | | 11/2007 |
| WO | WO 2008/019967 | | 2/2008 |
| WO | WO 2008/098892 | | 8/2008 |
| WO | WO 2008098892 A1 | * | 8/2008 |
| WO | WO 2010/012758 | | 2/2010 |

OTHER PUBLICATIONS

Bartoszyk et al., "Anxiolytic Effects of Dopamine Receptor Ligands: I. Involvement of Dopamine Autoreceptors" Life Sciences, Pergamon Press, Oxford, GB, vol. 62, No. 7, Jan. 1, 1998, pp. 649-663.
Benjamin, et al., Biochemical Pharmacology; vol. 72; No. 6; p. 770-782, 2006.
Bianchi "Current Issues in CNS drug" p. 1-3 (2011).
Binggeli et al., CA148:285064 (2008).
Braga et al., Roy. Soc. Chem. Chem. Commun. p. 3635-3645 (2005).
Cell Surface Receptor, Wikipedia, p. 1-6 (2012).
Contreras, Jean Marie, "Aminopyridazines as Acetylcholinesterase Inhibitors", J. Med. Chem. (1999),42 (4), 730-741.
Cook et al., CA132_347492 (2000).
Dean et al., J. Org. Chem. 1993, 58, 7916-7917.
Eichenberger, K.; Rometsch, R..; Druey, J. Australian Journal of Chemistry 1956, 9, 1755-1764. [See English abstract provided].
Fryatt et al., J. Bioorganic and Medicinal Chemistry, 2004, 12, 1667-1687.
Genin et al., "Synthesis and structure-activity relationships of the (alkylamino)piperidine-containing BHAP class of non-nucleoside reverse transcriptase inhibitors: effect of 3-alkylpyridine ring substitution" J. Med. Chem., vol. 42, No. 20, 1999, pp. 4140-4149.
Genin et al., "Synthesis and bioactivity of novel bis(heteroaryl)piperazine (BHAP) reverse transcriptase inhibitors: structure-activity relationships and increased metabolic stabilita of novel substituted pyri di ne' analogs" J. Med. Chem., vol. 39, No. 26, 1996, pp. 5267-5275.
Gillaspy et al., Tetrahedron Letters 1995, 36, 7399-7402.
Griesser, in Chapter 8, The Importance of Solvates (pp. 211-230), in the text, Polymorphism: In the Pharmaceutical Industry, Hilfiker, 2006.
Grundt et al., Bioorg. Med. Chem. Lett 17(3) 745-749 (2007).
Joyce et al., (2005) Dopamine D3 receptor antagonist as therapeutic agents. Drug Discovery Today 10: 917-925.
Kapitulnik, J., Frontiers in Pharm. p. 1-2, (2011).
Kapur, et al., "Does fast dissociation from the dopamine D2 receptor explain the action of atypical antipsychotics? A new hypothesis", Am. J. Psychiatry, 2001,158:3, p. 360-369.
Kikuchi et al., J. Med. Chem. (1999), 42 (4), 730-741.
Kortagere et al., "Certain 1,4-disubstituted aromati c piperidines and piperazines with extreme selectivity for the Dopamine D4 receptor interact with a common receptor microdomain" Molecular Pharmacology, vol. 66, No. 6, 2004, pp. 1491-1499.
Kula et al., "Neuropharmacological assessment of potential dopamine D4 receptor-selective radioligands" European Journal of Pharmacology, Amsterdam, NL, vol. 367, Jan. 1, 1999, pp. 139-142.
Kula et al., "RBI-257: A highly potent dopamine D receptor-selective ligand", European Journal of Pharmacology, 331 (1997), pp. 333-336.
Leysen, J., et al.,"The dissociation rate of unlabeled dopamine antagonists and agonists from the dopamine-D2 receptor, application of an original filter method", Journal of Receptor Research, 1984, 4(7), 817-845.
Moragues, J. et al., "Dopaminergic Activity in a series of n-substituted 2-aminopyrimidines" Farmaco, vol. 35, No. 11, 1980, pp. 951-964.
Munson et al., "Synthesis of 2-AlkYlamino-3-fluoropyridines Using Buchwald Conditions" Synthetic Communications, Taylor & Francis, Philadelphia, PA, vol. 34, No. 5, Jan. 1, 2004, pp. 759-766.
Okuyama et al., Life Sci. 65(20) 2109-2125 (1999).
Phedias et al., CA148:509885 (2008).
Schlachter et al. "Substituted 4-aminopiperidines having high in vitro affinity and selectivity for the cloned human dopami ne D4 receptor" European Journal of Pharmacology, vol. 322, 1997, pp. 283-286.
Seddon, K., Crystal. Growth & Design 4(6)1087 (2004).
Tao et al., Tetrahedron Lett. 2003, 44, 7993-7996.
TenBrink, CA124:8845 (1995).
Vippagunta et al., "Crystalline solids", Adv. Drug Delivery Reviews 48 (2001) 3-26.
Wood et al., Exp. Opin. Invest. Drugs 1696)771-775 (2007).
Xiao et al., Bioorg, Med. Chem. Lett. v.21, p. 861-864 (2011).
Yamada et al., Involvement of Septal and Striatal Dopamine D-2 Receptors in Yawning Behavior in Rats, Psychopharmacology, vol. 1, 1986, pp. 9-13.
Zablotskaya et al., Chem. Het. Compo v.38 (7), p. 859-866 (2002).
Zhang et al., Exp. Opin. Ther. Patents 16(5) 587-630 (2006).
Garzya et al., Bioorganic & Medicinal Chemistry Letters, 17 (2007) 400-405.
Kula et al., CA127:171455 (1997).
Liu et al., Drug Development Research, 70: 145-168 (2009).
Goodman et al., Tetrahedron 1999, 55, 15067-15070.
Holenz et al., Drug discovery today; vol. 11; No. 7-8; p. 283-299 (2006) Apr. 26, 2013.
Lovenberg et al., Cloning of rat histamine $H_3$ receptor reveals distinct species pharmacological profiles. J Pharmacol Expt Ther 2000;293:771-778.
Mitchell and Neumaier (2005) 5-$HT_6$ receptors: a novel target for cognitive enhancement. Pharmacology & Therapeutics 108:320-333.
Rodefer et al., Neurospychopharmacology (2008) 2657-2666.

* cited by examiner

SUBSTITUTED 6-(1-PIPERAZINYL)-PYRIDAZINES AS 5-HT$_6$ RECEPTOR ANTAGONISTS

CROSS REFERENCE TO RELATED APPLICATIONS

This application claims priority from and is the national stage of PCT Application No. PCT/EP2009/004745, filed Jul. 1, 2009, the entire disclosure of which is hereby incorporated by reference in its entirety, which claims priority from European Patent Application No. 08159591.0, filed Jul. 3, 2008.

FIELD OF THE INVENTION

The present invention is concerned with novel substituted 6-(1-piperazinyl)-pyridazines having 5-HT$_6$-antagonistic properties. The invention further relates to processes for preparing such novel compounds, pharmaceutical compositions comprising said novel compound as an active ingredient as well as the use of said compounds as a medicine.

BACKGROUND PRIOR ART

WO-2003/066604 relates amongst others to 3-aryl-6-piperazin-1-ylpyridazines with histamine H3 receptor activity which can be used in the treatment of narcolepsy.

DESCRIPTION OF THE INVENTION

The 5-hydroxytryptamine receptor 6 (5-HT$_6$) receptor belongs to the G-protein-coupled receptor family and is coupled to the Gs-family of G proteins, including the 5-HT$_4$ and 5-HT$_7$ receptor, that stimulate adenylate cyclase activity. The 5-HT$_6$ receptor also appears to regulate glutaminergic and cholinergic neuronal activity. 5-HT$_6$ receptors are selectively found in the brain areas involved in cognitive processes. The blockade of serotonin 5-HT$_6$ may be beneficial in higher cognitive processes such as memory and when negative symptoms associated with schizophrenia are considered.

Indeed, numerous preclinical data have shown that 5-HT$_6$ receptor antagonism has positive effects on cognitive processes in rodents (Mitchell and Neumaier (2005) 5-HT$_6$ receptors: a novel target for cognitive enhancement. Pharmacology & Therapeutics 108:320-333). The 5-HT$_6$ receptor has little or no expression in peripheral tissues, which may result in selectivity in drug targeting with fewer side effects.

More in general, compounds with 5-HT$_6$ receptor affinity may further be useful for the treatment of a variety of disorders of the Central Nervous System, anxiety, depression, attention deficit hyperactivity disorder, Alzheimer's disease, epilepsy, and schizophrenia.

In addition, 5-HT$_6$ antagonism has also been linked to appetite and food intake suppression. The prevalence of food ingestion disorders, like for example obesity, makes this a leading public health problem in all age groups. Food ingestion disorders predispose to various serious diseases such as diabetes, disorders of the gastrointestinal tracts, cardiovascular diseases, sleep apnea and osteoarthritis. The 5-HT$_6$ receptor has generated an enormous interest as a molecular target for the development of a new generation of safe and more effective anti-obesity drugs.

It is the object of the present invention to provide novel compounds that are selective 5-HT$_6$ receptor antagonists which have negligible interactions with other receptors resulting in fewer side-effects. The invention further relates to methods for their preparation and pharmaceutical compositions comprising them. The invention also relates to the use of these derivatives for the manufacture of a medicament for the treatment or prophylaxis of cognitive impairment and food related disorders.

The present invention concerns novel compounds according to Formula (I):

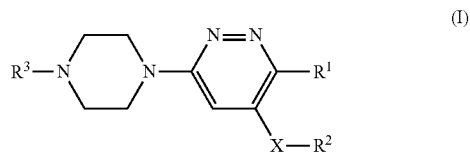

and stereoisomeric forms thereof, wherein
$R^1$ is chloro, trifluoromethyl or cyano;
$R^2$ is phenyl or phenyl substituted with halo;
$R^3$ is hydrogen, $C_{1-4}$-alkyl or pyridinylmethyl;
X is —O—, —NH—, —CH$_2$—, —CH(OH)—, —SO$_2$—, —CO—, —NH—CH$_2$—, —O—CH$_2$—, 1,2-ethenediyl or ethynediyl;
and the pharmaceutically acceptable addition salts, and solvates thereof.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

For example, the invention relates to compounds of Formula (I) and stereoisomeric forms thereof, wherein
$R^1$ is trifluoromethyl;
$R^2$ is phenyl or phenyl substituted with halo; preferably $R^2$ is phenyl substituted with halo;
$R^3$ is hydrogen, $C_{1-4}$-alkyl or pyridinylmethyl; preferably $R^3$ is hydrogen, methyl or pyridinylmethyl;
X is —O—, —NH—, —CH$_2$—, —CH(OH)—, —SO$_2$—, —CO—, —NH—CH$_2$—, —O—CH$_2$—, 1,2-ethenediyl or ethynediyl;
and the pharmaceutically acceptable addition salts, and solvates thereof.

The invention relates in particular to compounds of Formula (I) and stereoisomeric forms thereof, wherein
$R^1$ is trifluoromethyl;
$R^2$ is phenyl or phenyl substituted with fluoro;
$R^3$ is hydrogen, methyl or pyridinylmethyl;
X is —O—, —NH—, —CH$_2$—, —CH(OH)—, —SO$_2$—, —CO—, —NH—CH$_2$—, —O—CH$_2$—, 1,2-ethenediyl or ethynediyl;
and the pharmaceutically acceptable addition salts and solvates thereof.

In a further embodiment, the invention relates to compounds according to any of the other embodiments, wherein $R^2$ is phenyl or phenyl substituted with one or more substituents selected from the group consisting of halo.

In a further embodiment, the invention relates to compounds according to any of the other embodiments, wherein $R^2$ is phenyl or phenyl substituted with one, two or three substituents selected from the group consisting of halo.

In a further embodiment, the invention relates to compounds according to any of the other embodiments, wherein $R^2$ is phenyl or phenyl substituted with one halo.

In a further embodiment, the invention relates to compounds according to any of the other embodiments, wherein halo is fluoro.

Amongst the compounds of Formula (I) and the stereoisomeric forms thereof, the most interesting are, for example, 4-(4-fluorophenoxy)-6-(1-piperazinyl)-3-(trifluoromethyl)-pyridazine,
N-(4-fluorophenyl)-6-(1-piperazinyl)-3-(trifluoromethyl)-4-pyridazinamine,
4-(phenylmethyl)-6-(1-piperazinyl)-3-(trifluoromethyl)-pyridazine,
phenyl[6-(1-piperazinyl)-3-(trifluoromethyl)-4-pyridazinyl]-methanone,
alpha-phenyl-6-(1-piperazinyl)-3-(trifluoromethyl)-4-pyridazinemethanol,
4-(phenylsulfonyl)-6-(1-piperazinyl)-3-(trifluoromethyl)-pyridazine,
4-[(Z)-2-(4-fluorophenyl)ethenyl]-6-(1-piperazinyl)-3-(trifluoromethyl)-pyridazine,
4-[(E)-2-(4-fluorophenyl)ethenyl]-6-(1-piperazinyl)-3-(trifluoromethyl)-pyridazine,
4-[(4-fluorophenyl)ethynyl]-6-(1-piperazinyl)-3-(trifluoromethyl)-pyridazine,
6-(4-methyl-1-piperazinyl)-4-[(E)-2-phenylethenyl]-3-(trifluoromethyl)-pyridazine,
[6-(4-methyl-1-piperazinyl)-3-(trifluoromethyl)-4-pyridazinyl]phenyl-methanone,
N-[(4-fluorophenyl)methyl]-6-(1-piperazinyl)-3-(trifluoromethyl)-4-pyridazinamine,
4-[(4-fluorophenyl)methoxy]-6-(1-piperazinyl)-3-(trifluoromethyl)-pyridazine,
4-[(E)-2-phenylethenyl]-6-(1-piperazinyl)-3-(trifluoromethyl)-pyridazine,
N-(4-fluorophenyl)-6-(1-piperazinyl)-3-(trifluoromethyl)-4-pyridazinamine.2.5HCl.0.5H$_2$O,
4-[(E)-2-phenylethenyl]-6-[4-(4-pyridinylmethyl)-1-piperazinyl]-3-(trifluoromethyl)-pyridazine,
4-[(E)-2-phenylethenyl]-6-[4-(2-pyridinylmethyl)-1-piperazinyl]-3-(trifluoromethyl)-pyridazine,
and the pharmaceutically acceptable addition salts and solvates thereof.

The chemical names of the compounds of the present invention were generated according to the nomenclature rules agreed upon by the Chemical Abstracts Service (CAS). In case of tautomeric forms, the name of the depicted tautomeric form of the structure was generated. However it should be clear that the other non-depicted tautomeric form is also included within the scope of the present invention.

Whenever the term "substituted" is used in the present invention, it is meant to indicate that one or more hydrogens, preferably from 1 to 3 hydrogens, more preferably 1 hydrogen, on the atom indicated in the expression using "substituted" are replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent. For example, when phenyl is substituted with halo, this means that said phenyl is substituted with one or more substituents selected from halo.

Throughout this application, the term "$C_{1-4}$alkyl" defines straight or branched chain saturated hydrocarbon radicals having from 1 to 4 carbon atoms such as methyl, ethyl, propyl, 1-methylethyl, butyl, 1,1-dimethylethyl. The term halo as a group or part of a group is generic to fluoro, chloro, bromo, and iodo unless otherwise is indicated or is clear from the context.

When any variable occurs more than one time in any constituent, each definition is independent.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid. Conversely, said salts forms can be converted into the free forms by treatment with an appropriate base. The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropyl-amine, di-n-butylamine, pyrrolidine, piperidine, morpholine, trimethylamine, triethyl-amine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of formula (I) are able to form, as well as the salts thereof. Examples of such forms are e.g. hydrates, alcoholates and the like.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereoisomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereoisomeric forms may also be derived from the corresponding pure stereoisomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. In particular, when hydrogen is mentioned, it is understood to refer to $^1H$, $^2H$, $^3H$ and mixtures thereof.

A compound according to the invention therefore inherently comprises a compound with one or more isotopes of one or more elements, and mixtures thereof, including a radioactive compound, also called radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$ all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

The terms described above and others used in the specification are well understood to those in the art.

Pharmacology

In order to find compounds active for the treatment of cognitive impairment and food related disorders, we have screened for compounds selectively interacting with the serotonin 5-$HT_6$ receptor. The compounds within the scope of this invention, were found to have a clean profile, this is to have low affinity for the tested receptors, with the exception of the serotonin 5-$HT_6$ receptor.

Compounds of the present invention may further be expected to be active in the 'Reversal of subchronic PCP-induced attentional set shifting in rats' test (J. S. Rodefer et al., Neuropsychopharmacology (2007), 1-10).

In view of the aforementioned pharmacology of the compounds of Formula (I), it follows that they are suitable for use as a medicine.

More especially a medicine in the treatment or prevention of conditions wherein cognition is impaired; Alzheimer's disease, Parkinson's disease, Schizophrenia, Huntingdon's disease, Lewy Body Dementia, dementia due to HIV disease, dementia due to Creutzfeldt-Jakob disease; amnestic disorders; mild cognitive impairment; and age-related cognitive decline; for the treatment and/or prevention of feeding disorders and diseases, for the regulation of appetite; for the maintenance, increase or reduction of body weight; anorexia, bulimia, obesity, cachexia, type II diabetes (non insulin dependent diabetes mellitus), type II diabetes caused by obesity; for the treatment and/or prevention of stroke; migraine; head trauma; epilepsy; irritable colon syndrome; irritable bowel syndrome; for the treatment of disorders of the central nervous system; schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; trichotillomania; convulsive disorder; seizure; substance dependence; substance abuse; substance withdrawal; for the treatment and/or prevention of drug addiction and/or withdrawal; for the treatment and/or prevention of nicotine addiction and/or withdrawal; for the treatment and/or prevention of alcohol addiction and/or withdrawal.

To optimize treatment of patients suffering from a disorder as mentioned in the foregoing paragraph, the compounds of Formula (I) may be administered together with other psychotropic compounds.

The present invention also provides a method of treating warm-blooded animals suffering from such disorders, said method comprising the systemic administration of a therapeutic amount of a compound of Formula (I) effective in treating the above described disorders.

The present invention also relates to the use of compounds of Formula (I) as defined hereinabove for the manufacture of a medicament, more especially a medicine in the treatment and/or prevention of conditions wherein cognition is impaired; Alzheimer's disease, Parkinson's disease, Schizophrenia, Huntingdon's disease, Lewy Body Dementia, dementia due to HIV disease, dementia due to Creutzfeldt-Jakob disease; amnestic disorders; mild cognitive impairment; and age-related cognitive decline; for the treatment and/or prevention of feeding disorders and diseases, for the regulation of appetite; for the maintenance, increase or reduction of body weight; anorexia, bulimia, obesity, cachexia, type II diabetes (non insulin dependent diabetes mellitus), type II diabetes caused by obesity; for the treatment and/or prevention of stroke; migraine; head trauma; epilepsy; irritable colon syndrome; irritable bowel syndrome; for the treatment of disorders of the central nervous system; schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, Bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation; pervasive developmental disorders; attention deficit disorders, attention-deficit/hyperactivity disorder, disruptive behaviour disorders; personality disorder of the paranoid type, personality disorder of the schizoid type, personality disorder of the schizotypical type; tic disorders, Tourette's syndrome; trichotillomania; convulsive disorder; seizure; substance dependence; substance abuse; substance withdrawal; for the treatment and/or prevention of drug addiction and/or withdrawal; for the treatment and/or prevention of nicotine addiction and/or withdrawal; for the treatment and/or prevention of alcohol addiction and/or withdrawal.

In an embodiment, said conditions are selected from the treatment and/or prevention of drug addiction and/or withdrawal; the treatment and/or prevention of nicotine addiction and/or withdrawal; the treatment and/or prevention of alcohol addiction and/or withdrawal.

In an embodiment, said diseases or conditions are selected from conditions wherein cognition is impaired, disorders of the central nervous system, anxiety, depression, attention deficit hyperactivity disorder, Alzheimer's disease, epilepsy, schizophrenia, feeding disorders and diseases.

In an embodiment, said diseases or conditions are selected from conditions wherein cognition is impaired, disorders of the central nervous system, anxiety, depression, attention deficit hyperactivity disorder, Alzheimer's disease, epilepsy, and schizophrenia.

In an embodiment, said diseases or conditions are selected from conditions wherein cognition is impaired, anxiety, Alzheimer's disease, and schizophrenia.

In an embodiment, said diseases or conditions are selected from anxiety, Alzheimer's disease, and schizophrenia.

In an embodiment, said disease is schizophrenia.

In an embodiment, said disease is Alzheimer's disease.

In an embodiment, said condition is a condition wherein cognition is impaired.

The present invention also relates to the use of compounds of Formula (I) as defined hereinabove for the manufacture of a medicament, more especially a medicine in the treatment of said diseases or conditions.

The present invention also relates to compounds of Formula (I) for use in treating or preventing the diseases or conditions mentioned hereinbefore.

The present invention also relates to compounds of Formula (I) for use in treating the diseases or conditions mentioned hereinbefore.

The present invention also relates to compounds of Formula (I) for treating or preventing the diseases or conditions mentioned hereinbefore.

The present invention also relates to compounds of Formula (I) for treating the diseases or conditions mentioned hereinbefore.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.05 mg/kg to about 1 mg/kg body weight.

The invention also relates to a pharmaceutical composition comprising a pharmaceutically acceptable carrier and, as active ingredient, a therapeutically effective amount of a compound according to Formula (I).

For ease of administration, the subject compounds may be formulated into various pharmaceutical forms for administration purposes. The compounds according to the invention, in particular the compounds according to Formula (I), a pharmaceutically acceptable acid or base addition salt thereof, a stereoisomeric form thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

Preparation

Compounds of Formula (I-a),

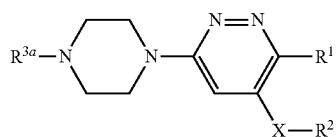

wherein $R^1$ is chloro, trifluoromethyl or cyano, $R^{3a}$ is $C_{1-4}$alkyl or pyridinylmethyl and where $R^2$ and X are defined as mentioned before, can be prepared by reacting a compound of Formula (I-b)

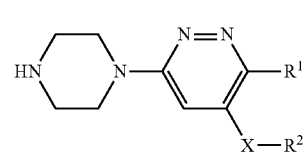

wherein $R^1$, X and $R^2$ are defined as mentioned before, with a $C_{1-4}$-aldehyde (such as e.g. formaldehyde or acetaldehyde) or pyridinecarboxaldehyde in the presence of a base such as $Et_3N$, a reducing agent such as $NaBH(OAc)_3$, Pt/C (not suitable for $R^{1a}$=Cl) or Raney Nickel (not suitable for $R^{1a}$=CN) and a suitable reaction solvent such as dichloromethane (DCM), methanol or ethanol.

Compounds of Formula (I-b)

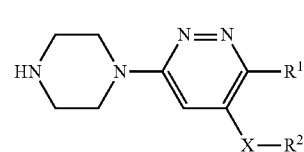

wherein the substituents are defined as mentioned before, may be prepared by deprotection of the protecting group in an intermediate of Formula (II),

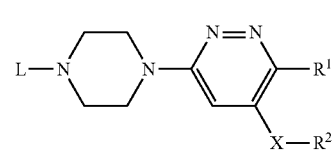

wherein L represents a suitable protecting group, such as tert-butyloxycarbonyl, and $R^1$, $R^2$ and X are defined as mentioned before, under suitable conditions, such as in the presence of trifluoroacetic acid (TFA) in DCM, or an acid cation-exchange resin of the sulphonated polystyrene type (e.g. AMBERLITE™ acid) in methanol (MeOH), or HCl in a solvent as dioxane.

Intermediates of Formula (II')

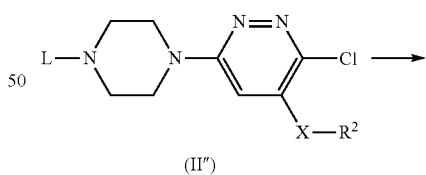

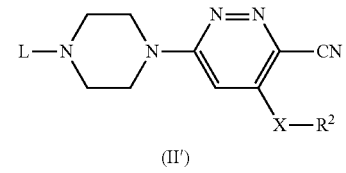

wherein L represents a suitable protecting group, such as tert-butyloxycarbonyl, and $R^2$ and X are defined as mentioned before, may be prepared by reacting the chloro derivative (II") with $Zn(CN)_2$ in the presence of a palladium catalyst such as tetrakis(triphenylphosphine)palladium in a suitable solvent such as for example DMF.

Intermediates of Formula (II-a)

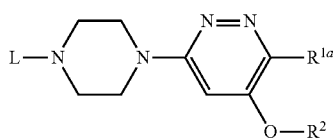

wherein $R^{1a}$ is chloro or trifluoromethyl and the other substituents are defined as hereabove, are generally prepared in a N,N-dimethylglycine-promoted Ullmann coupling reaction between an intermediate of Formula (III)

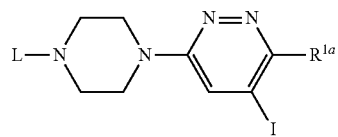

wherein $R^{1a}$ and L are as defined hereabove, with a commercially available $R^x$-phenol, wherein $R^x$ is hydrogen or halo. This type of reaction typically can be performed under copper or nickel catalysed conditions (for example using copper or nickel salts such as for example $Cu_2O$, CuI or $Ni(OAc)_2$) and a base like $Cs_2CO_3$, $K_3PO_4$ or $K_2CO_3$ at an elevated temperature (70-100° C.) in an appropriate inert solvent such as dioxane or toluene.

Intermediates of Formula (II-b)

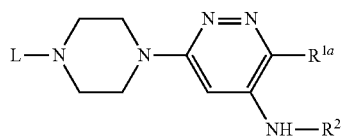

wherein $R^{1a}$, $R^2$ and L are defined as hereabove, are generally prepared by reaction of an intermediate of Formula (III) with a commercially available $R^x$-benzenamine, wherein $R^x$ is hydrogen or halo, typically in the presence of a ligand such as (1S)-[1,1'-Binaphthalene]-2,2'-diylbis[diphenylphosphine] ((S)-BINAP), and a base like $Cs_2CO_3$, $K_3PO_4$, $K_2CO_3$ or sodium tert-butoxide (tert-BuONa) at an elevated temperature (70-100° C.) in an appropriate inert solvent such as dioxane or toluene.

Intermediates of Formula (II-c)

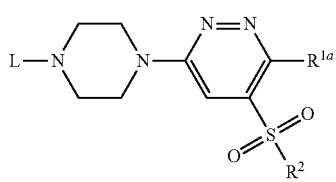

wherein $R^{1a}$, $R^2$ and L are defined as hereabove, are generally prepared by the CuI/L-proline catalysed coupling reaction of an intermediate of Formula (III) with a $R^x$-benzenesulfinic acid sodium salt, wherein $R^x$ is hydrogen or halo, in the presence of a base like $Cs_2CO_3$, $K_3PO_4$ or $K_2CO_3$ at an elevated temperature (70-100° C.) in an appropriate solvent such as dimethyl sulfoxide (DMSO).

Intermediates of Formula (II-d)

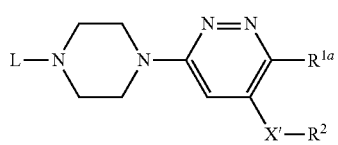

wherein $R^{1a}$, $R^2$ and L are defined as hereabove and where X' is 1,2-ethenediyl or ethynediyl are generally prepared by coupling of an intermediate of Formula (III) to [($R^x$-phenyl)ethenyl)]-boronic acid or ($R^x$-phenyl)ethynyl), wherein $R^x$ is hydrogen or halo, in the presence of a catalyst as tetrakis (triphenylphosphine)palladium ($Pd(PPh_3)_4$), a base like $Cs_2CO_3$, $K_3PO_4$ or $K_2CO_3$ and optionally copper or nickel salts such as, for example, $Cu_2O$, CuI or $Ni(OAc)_2$ optionally in the presence a suitable solvent such as dioxane or N,N-dimethylformamide (DMF), under suitable reaction conditions, such as a convenient temperature, either by conventional heating or under microwave irradiation for a period of time to ensure the completion of the reaction.

Intermediates of Formula (II-e)

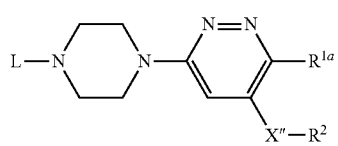

wherein $R^{1a}$, $R^2$ and L are defined as hereabove and wherein X" is —NH—$CH_2$— or —O—$CH_2$—, are generally prepared by coupling of an intermediate of Formula (III) to an $R^x$-benzenemethanamine or an $R^x$-benzenemethanol, wherein $R^x$ is hydrogen or halo, in the presence of a base like NaH in a suitable solvent such as THF or DMF, under suitable reaction conditions, such as a convenient temperature for a period of time to ensure the completion of the reaction.

Intermediates of Formula (II-f)

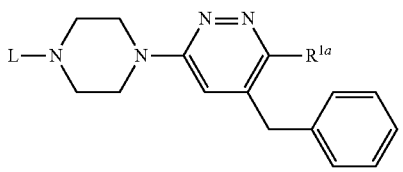

wherein $R^{1a}$ and L are defined as hereabove, may be prepared by the reduction of an intermediate of Formula (II-g)

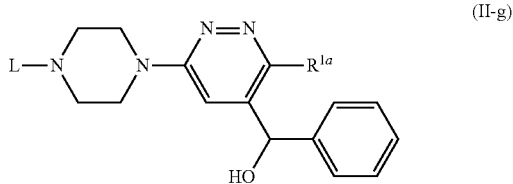

wherein $R^{1a}$ and L are defined as hereabove, with a Pd/C catalyst under $H_2$ atmosphere in an appropriate solvents such as EtOH or MeOH at room temperature.
Intermediates of Formula (II-h)

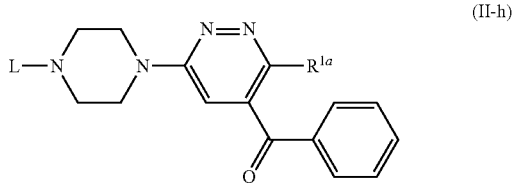

wherein $R^{1a}$ and L are defined as hereabove, may be prepared by the oxidation of an intermediate of Formula (II-g) with an oxidizing agent such as $MnO_2$ or 1,1,1-tris(acetyloxy)-3H-1,2-benziodoxol-3-one (Dess Martin's reagent) in a suitable solvent such as DCM or ethyl acetate (EtOAc) at low temperatures, typically at 0° C.
Intermediates of Formula (II-g) may be prepared by reacting a compound of Formula (IV)

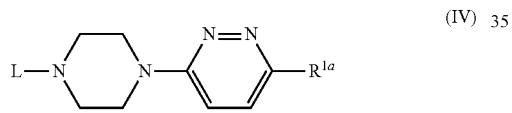

wherein $R^{1a}$ and L are defined as hereabove, with benzaldehyde in the presence of a suitable base such as a mixture of butyllithium and 2,2,6,6-tetramethylpiperidine in a suitable inert solvent such as tetrahydrofuran (THF) at low temperatures, typically ranging from −78° C. to 0° C.

Intermediates of Formula (III) may be prepared by reacting an intermediate of Formula (IV) with iodine in the presence of a suitable base such as a mixture of butyllithium and 2,2,6,6-tetramethylpiperidine in a suitable inert solvent such as THF at low temperatures, typically ranging from −78° C. to 0° C.
Intermediates of Formula (IV')

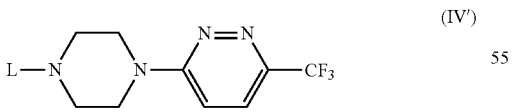

may be prepared by reacting 6-chloro-3-trifluoromethylpyridazine (prepared by following the procedure described in Goodman, A. J.; Stanforth, S. P; Tarbit B. Tetrahedron 1999, 55, 15067-15070) with tent-butyl 1-piperazinecarboxylate in the presence of a suitable base such as diisopropylethylamine (DIPEA) in a suitable solvent such as $CH_3CN$ at a convenient temperature, either by conventional heating or under microwave irradiation for a period of time to ensure the completion of the reaction.

The following examples illustrate the present invention.
Experimental Part

Hereinafter, the term "DCM" means dichloromethane, "MeOH" means methanol, "THF" means tetrahydrofuran, "LCMS" means Liquid Chromatography/Mass spectrometry, "q.s." means quantum sufficit, "HPLC" means high-performance liquid chromatography, "r.t." means room temperature, "Pd(OAc)$_2$" means palladium acetate, "DIPEA" means diisopropylethylamine, "min." means minutes, "h." means hours, "(S)-BINAP" means (1S)-[1,1'-Binaphthalene]-2,2'-diylbis[diphenylphosphine], "EtOAc" means ethyl acetate, "Et$_3$N" means triethylamine, "EtOH" means ethanol, "r.m." means reaction mixture, "DMSO" means dimethyl sulfoxide, "TFA" means trifluoroacetic acid, "Pd(PPh$_3$)$_4$" means tetrakis(triphenylphosphine)palladium, and "NaBH(OAc)$_3$" means sodium triacetoxyborohydride.

Microwave assisted reactions were performed in a single-mode reactor: Emrys™ Optimizer microwave reactor (Personal Chemistry A.B., currently Biotage).

$^1$H NMR spectra were recorded either on a Bruker DPX-400 or on a Bruker AV-500 spectrometer with standard pulse sequences, operating at 400 MHz and 500 MHz respectively, using CDCl$_3$ and DMSO-d$_6$ as solvents. Chemical shifts (δ) are reported in parts per million (ppm) downfield from tetramethylsilane (TMS), which was used as internal standard.
A. Preparation of the Intermediates

EXAMPLE A1 a) Preparation of Intermediate 1

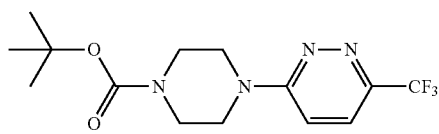

A mixture of 6-chloro-3-trifluoromethylpyridazine (0.666 g, 5.09 mmol) (prepared by following the procedure described in Goodman, A. J.; Stanforth, S. P; Tarbit B. Tetrahedron 1999, 55, 15067-15070), tert-butyl 1-piperazinecarboxylate (1.138 g, 6.11 mmol) and DIPEA (1.95 ml, 1.12 mmol) in CH$_3$CN (10 ml) was stirred at 180° C. for 30 min. under microwave irradiation. The solvent was evaporated in vacuo and the residue was purified by column chromatography (silica gel; hexane/EtOAc) to yield intermediate 1 (1.67 g, 99%) as a light yellow solid. C$_{14}$H$_{19}$F$_3$N$_4$O$_2$ requires 332; Found 333 (MH$^+$).

b) Preparation of Intermediate 2

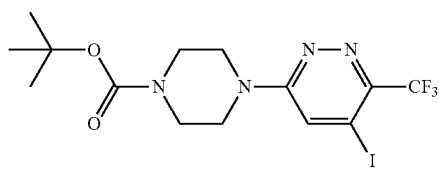 [SMILES: CC(C)(C)OC(=O)N1CCN(c2cc(I)c(C(F)(F)F)nn2)CC1]

2,2,6,6-Tetramethylpiperidine (3.808 ml, 22.56 mmol) was added to a mixture of butyllithium (2.5 M in hexanes) (6.31 ml, 15.79 mmol) in THF (125 ml) at 0° C. The r.m. was stirred at r.t. for 1 h. The mixture was cooled to −78° C. and then a solution of intermediate 1 (2.5 g, 7.52 mmol) in THF (20 ml) was added. The mixture was stirred for 1 h. at −78° C. before adding a solution of iodine (2.29 g, 9.024 mmol) in THF (10 ml). The mixture was stirred at −78° C. for 1 h. and then diluted with a 10% solution of acetic acid in THF. Subsequently, the mixture was allowed to reach r.t. and the solvent was evaporated in vacuo. The residue was diluted with DCM and extracted with water. The organic layer was separated, dried (MgSO$_4$), filtered and the solvent was evaporated in vacuo. The residue was precipitated from diethyl ether to yield intermediate 2 (2.81 g, 82%) as a light yellow solid. $C_{14}H_{18}F_3IN_4O_2$ requires 458; Found 459 (MH$^+$).

Intermediate 5

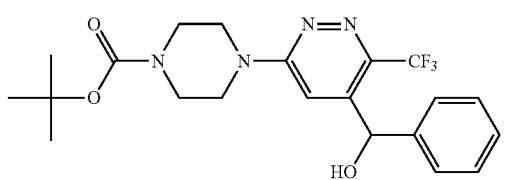 [SMILES: CC(C)(C)OC(=O)N1CCN(c2cc(C(O)c3ccccc3)c(C(F)(F)F)nn2)CC1]

was prepared according to an analogous protocol as intermediate 2, but benzaldehyde was used instead of iodine. Yield: 84%.

c-1) Preparation of Intermediate 3

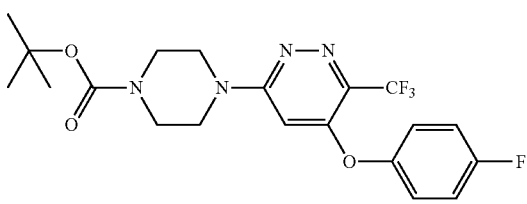 [SMILES: CC(C)(C)OC(=O)N1CCN(c2cc(Oc3ccc(F)cc3)c(C(F)(F)F)nn2)CC1]

A mixture of intermediate 2 (0.490 g, 1.069 mmol), 4-fluorophenol (0.215 g, 1.92 mmol), N,N-dimethylglycine (0.107 mmol), CuI (0.0061 g, 0.032 mmol) and Cs$_2$CO$_3$ (0.697 g, 2.14 mmol) in dioxane (5 ml) was flushed with N$_2$ and heated at 100° C. for 16 hours. Subsequently, the mixture was cooled and DCM, H$_2$O and a concentrated NH$_4$OH solution was added. The mixture was extracted and the separated organic layers were filtered over cotton. The solvent was evaporated and the residue was purified by flash column chromatography over silica gel (eluent: DCM/EtOAc 0-1-2-5%). The desired fractions were collected and the solvent was evaporated to yield 0.435 g (92%) of intermediate 3 as a white solid.

c-2) Preparation of Intermediate 4

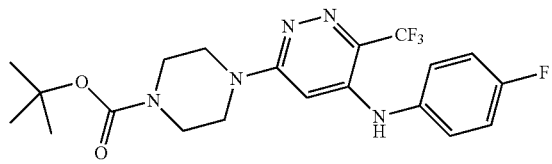 [SMILES: CC(C)(C)OC(=O)N1CCN(c2cc(Nc3ccc(F)cc3)c(C(F)(F)F)nn2)CC1]

A mixture of intermediate 2 (0.15 g, 0.327 mmol), 4-fluorobenzenamine (0.034 ml, 0.3 mmol), (S)-BINAP (0.0061 g, 0.009 mmol), Pd(OAc)$_2$ (0.002 g, 0.009 mmol), Cs$_2$CO$_3$ (0.533 g, 1.63 mmol) and Et$_3$N (0.002 ml, 0.02 mmol) in toluene (2 ml) was stirred and heated at 100° C. for 24 h. Subsequently, the mixture was cooled, filtered through diatomaceous earth (CELITE™) and the organic layer was evaporated. The residue was purified by flash column chromatography over silica gel ((eluent: DCM/EtOAc 100/0-97/3-95/5). The desired fractions were collected and the solvent was evaporated yielding 0.117 g (81%) of intermediate 4 as a yellow solid.

c-3) Preparation of Intermediate 7

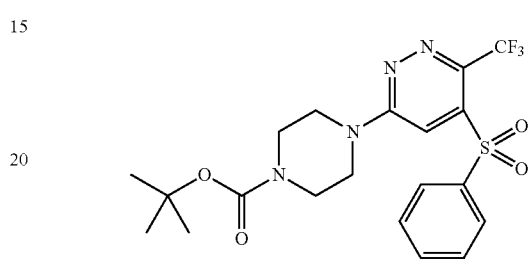

A solution of intermediate 2 (0.200 g, 0.0004 mol) in DMSO (1.5 ml; dry) was flushed with N$_2$ for a few min. Then a mixture of benzenesulfinic acid sodium salt (0.143 g, 0.0009 mol), L-proline (0.020 g, 0.0002 mol), CuI (0.08 g) and K$_3$PO$_4$ (0.093 g, 0.0004 mol) were added to the solution and the r.m. was heated at 85° C. for 18 h. Subsequently, the mixture was diluted with DCM and the resulting mixture was washed with an aqueous solution of ammonia. The organic layer was separated, dried (MgSO$_4$), filtered and the filtrate was evaporated. The residue was purified by flash chromatography (eluent: DCM/(NH$_3$ 7N solution in MeOH) first 100/0 then 90/10). The desired fractions were collected and the solvent was evaporated. Yield: 0.148 g of intermediate 7 (72%) as a pale yellow solid.

c-4) Preparation of Intermediate 8

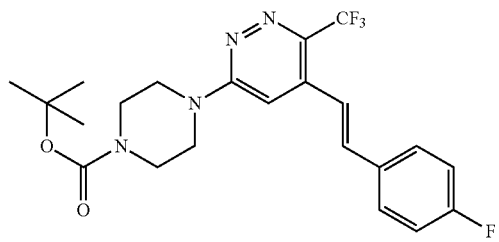

mixture of E/Z

A mixture of intermediate 2 (0.2 g, 0.00043 mol), [2-(4-fluorophenyl)vinyl]boronic acid (0.092 g, 0.00055 mol), Pd(PPh$_3$)$_4$ (0.015 g, 0.0000086 mol), K$_2$CO$_3$ (0.118 g, 0.000129 mol), dioxane (2 ml) and DMF (0.5 ml) was irradiated at 160° C. for 1 h under microwave irradiation. Then the solvent was evaporated and the residue was purified by flash column chromatography over silica gel (eluent: DCM/(NH$_3$ 7N solution in MeOH) 97/3). The desired fractions were collected and the solvent was evaporated. Yield: 0.179 g of intermediate 8 (92%; mixture of E/Z) as a yellow oil.

Intermediate 10

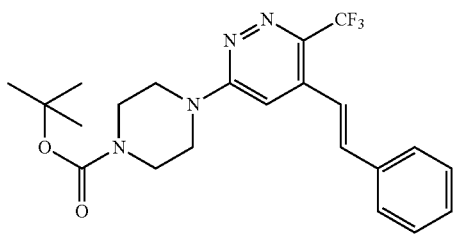

was prepared according to an analogous protocol as was used for the synthesis of intermediate 8, but (E)-(2-phenylvinyl)boronic acid was used as the starting material instead of [2-(4-fluorophenyl)vinyl]boronic acid.

c-5) Preparation of Intermediate 9

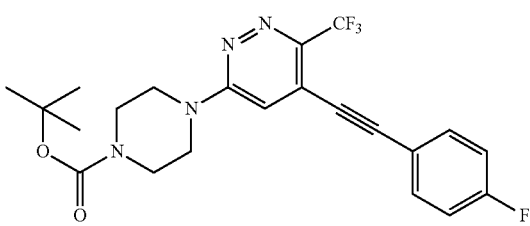 [SMILES: CC(C)(C)OC(=O)N1CCN(c2cc(C#Cc3ccc(F)cc3)c(C(F)(F)F)nn2)CC1]

A mixture of intermediate 2 (0.2 g, 0.43 mmol), 1-ethynyl-4-fluorobenzene (0.067 g, 0.55 mmol), Pd(PPh$_3$)$_4$ (0.010 g, 0.0086 mmol), CuI (0.002 g, 0.129 mmol) and Et$_3$N (2 ml) was stirred at 55° C. for 3 h. Then, the mixture was cooled, filtered through diatomaceous earth (CELITE™) and the filtrate was evaporated. The residue was purified by flash column chromatography over silicagel (eluent: DCM/(NH$_3$ 7N solution in MeOH) 97/3). The desired fractions were collected and the solvent was evaporated. Yield: 0.132 g of intermediate 9 (68%).

c-6) Preparation of Intermediate 12

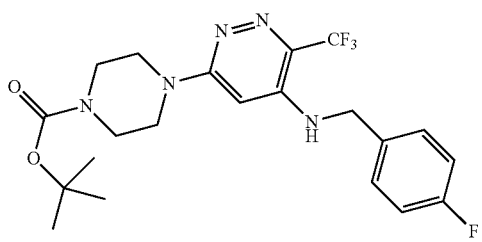 [SMILES: CC(C)(C)OC(=O)N1CCN(c2cc(NCc3ccc(F)cc3)c(C(F)(F)F)nn2)CC1]

A mixture of intermediate 2 (0.400 g, 0.873 mmol) and 4-fluorobenzenemethanamine (1.2 ml, 10.5 mmol) was stirred for 1 h. at 150° C. Subsequently, water, a saturated NH$_4$Cl solution and DCM were added. The organic layers were separated and were filtered over cotton. The filtrate was evaporated and the residue was purified by flash column chromatography over silica gel (eluent: DCM/EtOAc 100/0-95/5). The desired fractions were collected and the solvent was evaporated. Yield: 0.340 g of intermediate 12 (86%).

c-7) Preparation of Intermediate 13

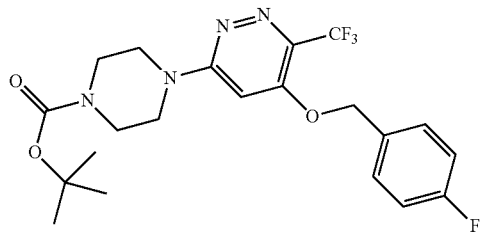 [SMILES: CC(C)(C)OC(=O)N1CCN(c2cc(OCc3ccc(F)cc3)c(C(F)(F)F)nn2)CC1]

4-Fluorobenzenemethanol (0.19 ml, 1.74 mmol) was added to a mixture of NaH (0.062 g, 1.55 mmol; 60% in oil) and DMF (4 ml; anhydrous). This mixture was stirred for 10 min. and then intermediate 2 (0.400 g, 0.873 mmol) in DMF (2 ml; anhydrous) was added. The r.m. was stirred for 1 h. at r.t. Subsequently, a saturated NH$_4$Cl solution, water and DCM were added. The organic layer was separated and was filtered over cotton. The filtrate was evaporated and the residue was purified by flash column chromatography (eluent: DCM/EtOAc 100/0-98/2-96/4). The desired fractions were collected and the solvent was evaporated. Yield: 0.295 g of intermediate 13 (74%).

EXAMPLE 2

Preparation of Intermediate 6

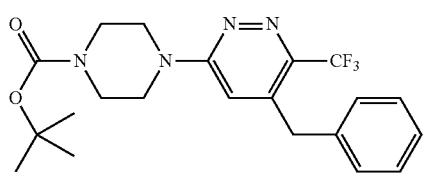 [SMILES: CC(C)(C)OC(=O)N1CCN(c2cc(Cc3ccccc3)c(C(F)(F)F)nn2)CC1]

Intermediate 5 (0.06 g, 0.0001 mol) was dissolved in EtOH (5 ml) and Pd/C (0.005 g) was added to this solution. The r.m. was stirred at r.t. and atmospheric pressure under H$_2$ atmosphere for 2 days. Then the mixture was filtered through a pad of diatomaceous earth (CELITE™) and the filtrate was evaporated. The residue was purified by column chromatography (eluent: DCM). The desired fractions were collected and the solvent was evaporated. Yield: 0.050 g of intermediate 6 (86%).

EXAMPLE A3 a) Preparation of Intermediate 11

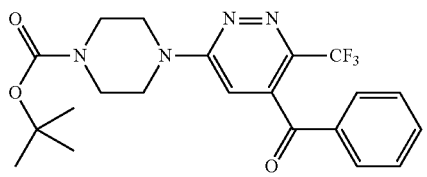 [SMILES: CC(C)(C)OC(=O)N1CCN(c2cc(C(=O)c3ccccc3)c(C(F)(F)F)nn2)CC1]

Intermediate 5 (0.08 g, 0.00018 mol) was dissolved in DCM (2 ml) and the solution was cooled down to 0° C. 1,1,1-Tris(acetyloxy)-3H-1,2-benziodoxol-3-one (Dess Martin's reagent) (0.12 g, 0.00027 mol) was added to this solution and the r.m. was stirred at 0° C. for 1 h. Subsequently, water was added and the layers were separated. The organic layer was dried ($Na_2SO_4$), filtered and the solvent was evaporated. Yield: Intermediate 11 (crude, used as such in the next reaction step).

b) Preparation of Intermediate 11 (Alternative Reaction Procedure)

$MnO_2$ (5 g, 0.058 mol) was added to a mixture of intermediate 5 (3 g, 0.007 mol) in EtOAc (60 ml). The r.m. was stirred overnight at r.t. Then the mixture was filtered and the solvent was evaporated to yield 2.5 g of intermediate 11 (83%; crude, used as such in the next reaction step).

B. Preparation of the Compounds

EXAMPLE B1

Preparation of Compound 1

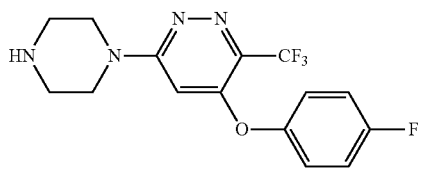

A mixture of intermediate 3 (0.435 g, 0.983 mmol) in TFA (2 ml) and DCM (18 ml) was stirred for 3 hours at r.t. Then DCM, a saturated $Na_2CO_3$ solution and $H_2O$ were added and the mixture was extracted. The separated organic layers were filtered over cotton, the solvent was evaporated and the residue was purified by flash column chromatography over silica gel (DCM/($NH_3$ 7 N solution in MeOH) 100/0-98/2). The desired fractions were collected and the solvent was evaporated to yield 0.316 g (94%) of compound 1.

$^1$H NMR (400 MHz, CDCl$_3$) δ ppm: 2.86-3.06 (m, 4 H) 3.57-3.64 (m, 4 H) 5.96 (s, 1 H) 7.08-7.25 (m, 4 H).

EXAMPLE B2 a-1) Preparation of Compound 2

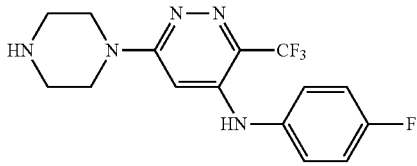

A mixture of intermediate 4 (0.117 g, 0.33 mmol) and an acid cation-exchange resin of the sulphonated polystyrene type (AMBERLITE™ acid) (q.s.) in MeOH (8 ml) was shaken for 24 h. The resin was filtered off and the organic layer was discarded. Subsequently, the resin was washed with MeOH and stirred for 30 min. in a $NH_3$ 7N solution in MeOH. The resin was filtered off and the obtained organic layer was concentrated in vacuo. The residue was purified by flash column chromatography over silica gel (DCM/MeOH 70/30). The desired fractions were collected and the solvent was evaporated to yield a yellow solid. This solid was repurified by HPLC to yield 0.048 g (53%) of a white solid. The amorphous solid was recrystallized from ethyl ether to yield 0.015 g of compound 2 (free base) as a crystalline white solid.

$^1$H NMR (400 MHz, DMSO-d$_6$) ppm 2.81-2.93 (m, 4 H) 3.47-3.53 (m, 4 H) 6.15 (s, 1 H) 7.26 (t, J=8.81 Hz, 2 H) 7.30-7.39 (m, 2 H) 8.13 (s, 1 H).

a-2) Preparation of Compound 16

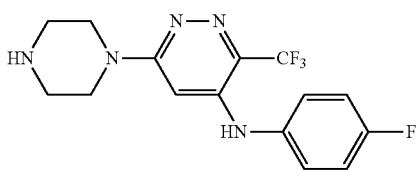 [SMILES: Fc1ccc(Nc2cc(N3CCNCC3)nnc2C(F)(F)F)cc1]

•2.5HCl•0.5H$_2$O

A mixture of intermediate 4 (0.425 g, 0.963 mmol), DCM (18 ml) and TFA (2 ml) was stirred for 3 h. at r.t. Then DCM, saturated $Na_2CO_3$ and $H_2O$ were added and the mixture was extracted. The separated organic layers were filtered over cotton and the solvent was evaporated. The residue was purified by flash chromatography over silica gel (eluent: DCM/($NH_3$ 7N solution in MeOH) from 100/0 till 97/3). The desired fractions were collected and the solvent was evaporated. The residue was dissolved in EtOAc/DIPE and a HCl solution in 2-propanol (5-6 N) was added. Subsequently, the major part of the solvent was evaporated. Extra EtOAc was added to the concentrate and sonication in an ultrasonic bath was applied to the mixture. The precipitate was filtered off and dried. Yield: 0.388 g of compound 16 (97%; .2.5HCl.0.5H$_2$O).

$^1$H NMR (400 MHz, DMSO-d$_6$) δ ppm 3.14 (br. s., 4 H) 3.71-3.79 (m, 4 H) 6.28 (s, 1 H) 7.28 (t, J=8.79 Hz, 2 H) 7.32-7.42 (m, 2 H) 8.47 (s, 1 H) 9.43 (br. s., 2 H).

b) Preparation of Compounds 7 and 8

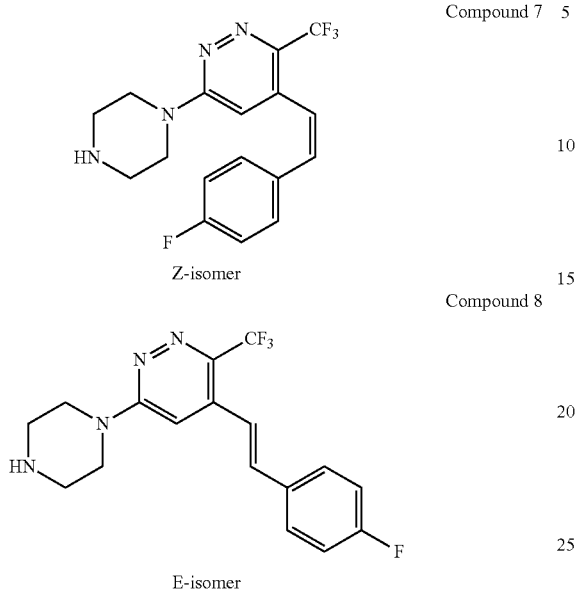

Z-isomer
Compound 7

Compound 8

E-isomer

Compound 7 (Z-isomer) and compound 8 (E-isomer) were prepared according to an analogous protocol as was used for the synthesis of compound 2, but intermediate 8 (mixture of E/Z) was used as the starting material instead of intermediate 4. After the HPLC purification, two pure isomers were obtained.

Compound 7:

$^1$H NMR (400 MHz, DMSO-$d_6$) δ ppm: 2.59-2.82 (m, 4 H) 3.45-3.57 (m, 4 H) 6.59 (br. d, J=12.4 Hz, 1 H) 6.91 (s, 1 H) 6.96 (d, J=12.4 Hz, 1 H) 7.04-7.25 (m, 4 H).

Compound 8:

$^1$H NMR (400 MHz, DMSO-$d_6$) δ ppm 2.75-2.88 (m, 4 H) 3.65-3.77 (m, 4 H) 7.05 (dd, J=16.17, 1.87 Hz, 1 H) 7.24-7.34 (m, 2 H) 7.53 (s, 0 H) 7.64-7.76 (m, 3 H).

c) Preparation of Compound 9

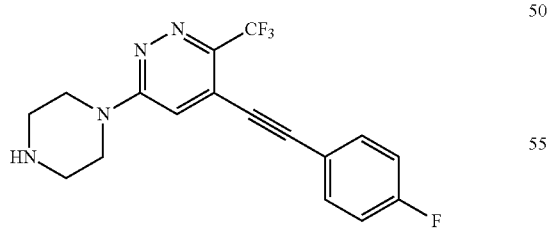

Compound 9 was prepared according to an analogous protocol as was used for the synthesis of compound 2, but intermediate 9 was used as the starting material instead of intermediate 4. Yield: Compound 9 as a yellow solid (80%).

$^1$H NMR (400 MHz, DMSO-$d_6$) δ ppm: 2.72-2.86 (m, 4 H) 3.63-3.75 (m, 4 H) 7.31-7.41 (m, 2 H) 7.60 (s, 1 H) 7.62-7.69 (m, 2 H).

EXAMPLE B3 a) Preparation of Compound 3

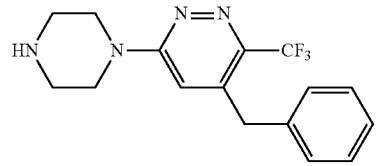

Intermediate 6 (0.05 g, 0.0001 mol) was dissolved in HCl 4M in dioxane (1 ml). The solution was stirred for 1 h. at r.t. The solvent was evaporated and the residue was dissolved in DCM. This solution was washed with a saturated NaHCO$_3$ solution, dried (Na$_2$SO$_4$) and filtered. The compound was purified by normal phase column chromatography (eluent: DCM/(NH$_3$ 7N solution in MeOH)). The desired fractions were collected and the solvent was evaporated yielding 0.035 g of compound 3 (90%).

$^1$H NMR (500 MHz, CDCl$_3$) δ ppm 2.82-2.89 (m, 4 H) 3.42-3.61 (m, 4 H) 3.98 (s, 2 H) 6.32 (s, 1 H) 7.09 (d, J=7.51 Hz, 2 H) 7.20-7.26 (m, 1 H) 7.29 (t, J=7.37 Hz, 2 H).

b) Preparation of Compound 5

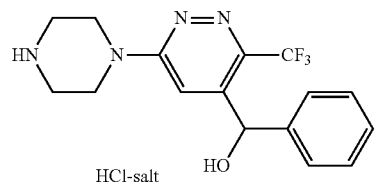 [SMILES: OC(c1ccccc1)c1cc(N2CCNCC2)nnc1C(F)(F)F]

HCl-salt

A solution of intermediate 5 (0.054 g, 0.109 mmol) and a 4M HCl solution in dioxane was stirred at r.t. for 16 h. The solvent was evaporated and the residue was treated with ethyl ether to yield a light yellow precipitate that was filtered off. Yield: 0.0426 g of compound 5 (92%; HCl-salt).

$^1$H NMR (400 MHz, DMSO-$d_6$) δ ppm: 3.18-3.32 (m, 4 H) 3.82-4.20 (m, 4 H) 5.87 (s, 1 H) 7.14-7.43 (m, 5 H) 7.65 (s, 1H) 9.07 (br. s., 2H).

EXAMPLE 4 a) Preparation of Compound 4 and Compound 12

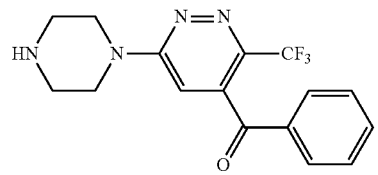

Compound 4 (free base)
Compound 12 (HCl-salt)

Intermediate 11 (crude; the residue that was obtained in example A3.a was dissolved in a 4M HCl solution in dioxane (2 ml) and the mixture was stirred at r.t. for 1 h. The solvent was evaporated and the residue was treated with a saturated NaHCO$_3$ solution, extracted with DCM and purified by column chromatography (eluent: DCM/EtOAc 7/3. The desired fractions were collected and the solvent was evaporated. Yield: 0.030 g of compound 4 (50%).

The HCl-salt of compound 4, compound 12, was obtained by dissolving intermediate 11 (0.5 g, 0.001145 mol) in a HCl solution in MeOH (15 ml). The r.m. was stirred for 4 h. at r.t. Then the solvent was evaporated to yield 0.350 g of compound 12 (81.9%; HCl-salt form).

b) Preparation of Compound 13

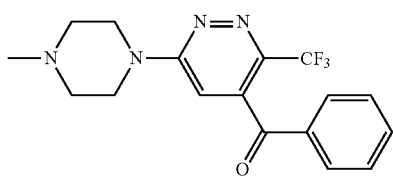 [SMILES: CN1CCN(c2cc(C(=O)c3ccccc3)c(C(F)(F)F)nn2)CC1]

A mixture of compound 12 (0.080 g, 0.215 mmol), formaldehyde (0.050 g, 0.47 mmol), NaBH(OAc)$_3$ (0.100 g, 0.47 mmol) and Et$_3$N (0.1 g, 1 mmol) in DCM (5 ml) was stirred overnight at r.t. Subsequently, the mixture was washed with a saturated NaHCO$_3$ solution. The separated organic layer was dried (Na$_2$SO$_4$), filtered and the solvent was evaporated in vacuo. The residue was purified by preparative TLC (eluent: DCM/MeOH 20/1). Yield: Compound 13 (42%).

EXAMPLE B5 a) Preparation of Compound 6

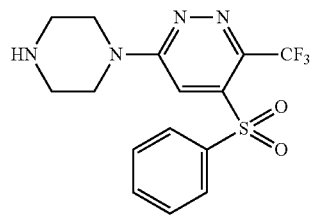 [SMILES: O=S(=O)(c1ccccc1)c1cc(N2CCNCC2)nnc1C(F)(F)F]

TFA (1 ml) was added to a solution of intermediate 7 (0.145 g, 0.0003 mol) in DCM (4 ml) and the r.m. was stirred for 2 h. at r.t. Subsequently, the solvent was evaporated and the residue was dissolved in DCM. This organic solution was washed with a saturated Na$_2$CO$_3$ solution. The organic layer was separated, dried (MgSO$_4$), filtered and the filtrate was evaporated. The product was purified by flash column chromatography (eluent: DCM/(NH$_3$ 7N solution in MeOH) first 100/0 then 95/5). The desired fractions were collected and the solvent was evaporated, to yield 0.103 g of a pale yellow solid. This solid was further purified by HPLC to yield 0.0513 g of compound 6 (45%) as a pale yellow solid.

$^1$H NMR (400 MHz, CDCl$_3$) δ ppm 2.96-3.08 (m, 4 H) 3.80-3.89 (m, 4 H) 7.45 -7.54 (m, 2 H) 7.58-7.64 (m, 1 H) 7.66 (s, 1 H) 7.79 (d, J=7.88 Hz, 2 H).

b) Preparation of Compound 14

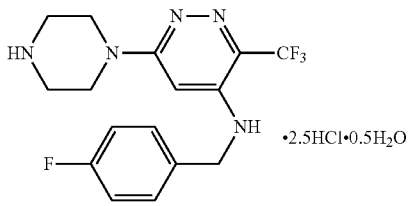 [SMILES: Fc1ccc(CNc2cc(N3CCNCC3)nnc2C(F)(F)F)cc1]

A mixture of intermediate 12 (0.340 g, 0.7465 mmol), TFA (1 ml) and DCM (9 ml) was stirred for 3 h. at r.t. Then a saturated Na$_2$CO$_3$ solution, water and DCM were added. The organic layer was separated and filtered over cotton. The solvent was evaporated and the residue was purified by flash column chromatography over silica gel (eluent: DCM/(NH$_3$ 7N solution in MeOH) first 100/0, then 99/1, then 98/2). The desired fractions were collected and the solvent was evaporated. The sticky product was treated with 5-6 N HCl in 2-propanol (0.5 ml). The solvent was evaporated and EtOAc was added to the residue. Sonication in an ultrasonic bath was applied to the mixture and subsequently the compound was filtered off and dried. Yield: 0.275 g of compound 14 (86%;. 2.5HCl.0.5H$_2$O).

$^1$H NMR (400 MHz, DMSO-d$_6$) δ ppm 3.17 (br. s., 4 H) 3.80-3.92 (m, 4 H) 4.59 (d, J=6.01 Hz, 2 H) 6.36 (s, 1 H) 7.18 (t, J=8.79 Hz, 2 H) 7.44 (dd, J=8.67, 5.66 Hz, 2 H) 7.85 (br. s., 1 H) 9.51 (br. s., 2 H).

c) Preparation of Compound 15

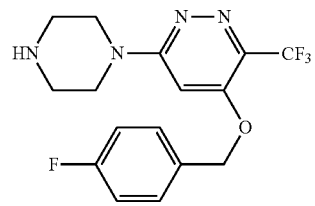 [SMILES: Fc1ccc(COc2cc(N3CCNCC3)nnc2C(F)(F)F)cc1]

Compound 15 was prepared according to an analogous protocol as was used for the synthesis of compound 6, but intermediate 13 was used as the starting material instead of intermediate 7. Yield: Compound 15 (88%).

$^1$H NMR (400 MHz, CDCl$_3$) δ ppm: 2.93-3.04 (m, 4 H) 3.62-3.76 (m, 4 H) 5.15 (s, 2 H) 6.23 (s, 1 H) 7.10 (t, J=8.67 Hz, 2 H) 7.38 (dd, J=8.55, 5.32 Hz, 2 H).

EXAMPLE B6 a) Preparation of Compound 10

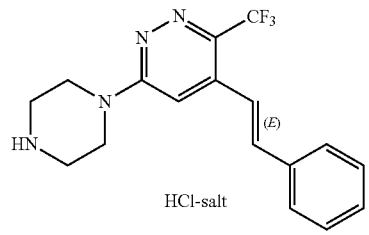 [SMILES: FC(F)(F)c1nnc(N2CCNCC2)cc1/C=C/c1ccccc1]

A mixture of intermediate 10 (5.5 g, 0.0127 mol) and a HCl solution in MeOH (110 ml) was stirred for 4 h. at r.t. Subsequently, the solvent was evaporated to yield 4.5 g of compound 10 (95%; HCl-salt).

b) Preparation of Compound 11

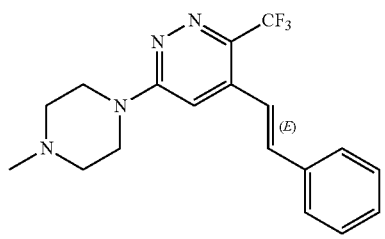 [SMILES: CN1CCN(c2cc(/C=C/c3ccccc3)c(C(F)(F)F)nn2)CC1]

A mixture of compound 10 (0.080 g, 0.22 mmol), formaldehyde (0.25 mmol), NaBH(OAc)$_3$ (q.s.) and Et$_3$N (0.101 g, 1 mmol) in DCM (5 ml) was stirred overnight at r.t. Then the solvent was evaporated and the residue was purified by preparative TLC (eluent: DCM/MeOH 20/1) to yield compound 11.

The following compounds of formula (I), as depicted in Table 1, were prepared by analogy to the above examples (Ex. No.). Some compounds were obtained as salt forms. In case the exact stoichiometry was determined, the result is shown in the column 'Salt forms', for example see Co. No. 14 and 16. In case the exact stoichiometry was not determined, only the type of salt form of the compound is indicated, for example see Co. No. 5.

TABLE 1

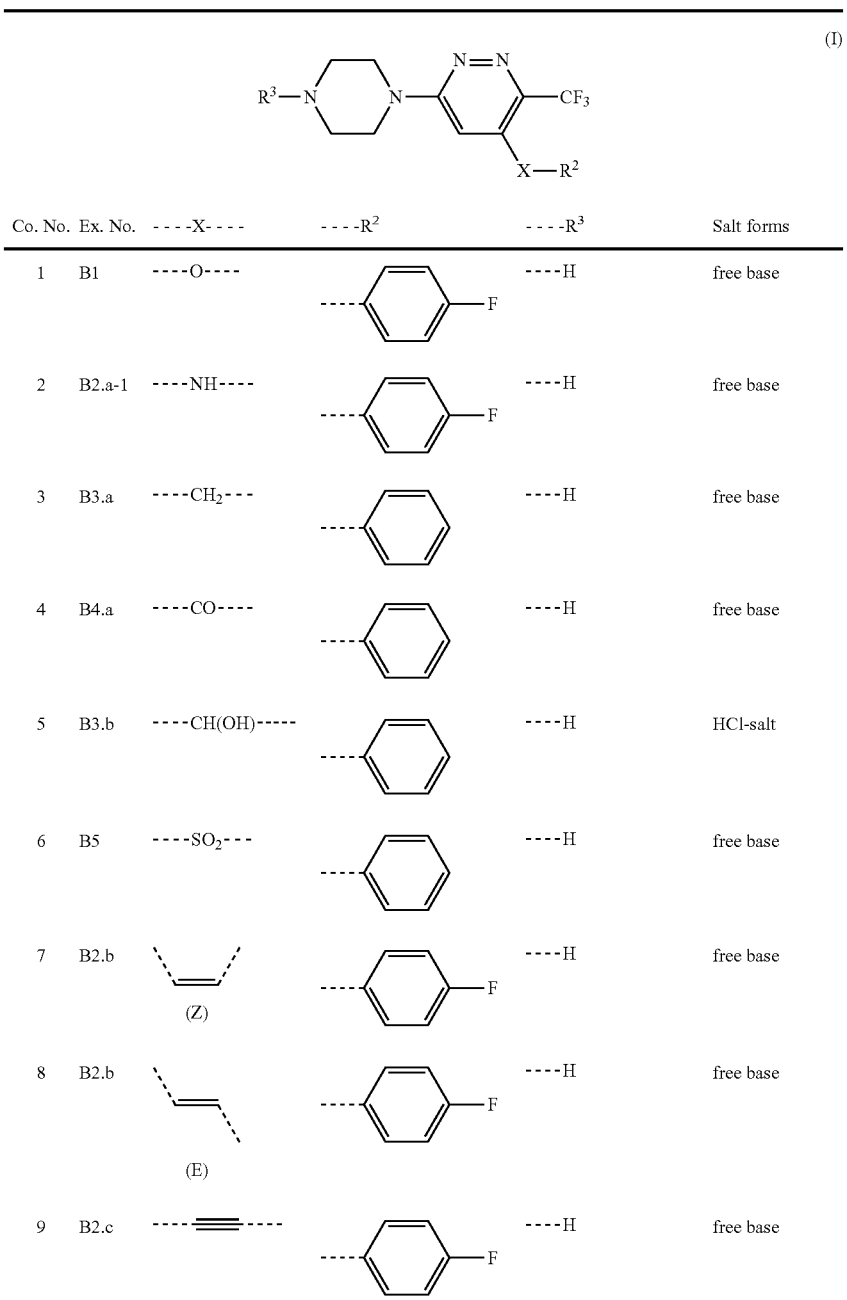

| Co. No. | Ex. No. | -X- | -R² | -R³ | Salt forms |
|---|---|---|---|---|---|
| 1 | B1 | -O- | 4-F-phenyl | -H | free base |
| 2 | B2.a-1 | -NH- | 4-F-phenyl | -H | free base |
| 3 | B3.a | -CH₂- | phenyl | -H | free base |
| 4 | B4.a | -CO- | phenyl | -H | free base |
| 5 | B3.b | -CH(OH)- | phenyl | -H | HCl-salt |
| 6 | B5 | -SO₂- | phenyl | -H | free base |
| 7 | B2.b | -CH=CH- (Z) | 4-F-phenyl | -H | free base |
| 8 | B2.b | -CH=CH- (E) | 4-F-phenyl | -H | free base |
| 9 | B2.c | -C≡C- | 4-F-phenyl | -H | free base |

TABLE 1-continued

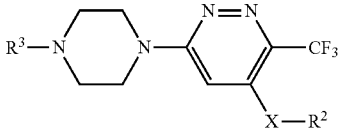

(I)

| Co. No. | Ex. No. | ----X---- | ----R² | ----R³ | Salt forms |
|---|---|---|---|---|---|
| 10 | B6.a | 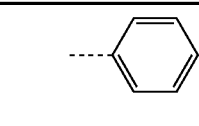 (E) | 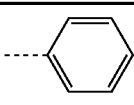 | ----H | HCl-salt |
| 11 | B6.b | 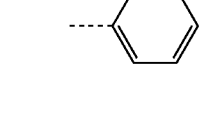 (E) | 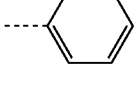 | ----CH₃ | free base |
| 12 | B4.a | ----CO---- | 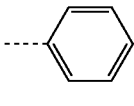 | ----H | HCl-salt |
| 13 | B4.b | ----CO---- | 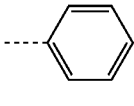 | ----CH₃ | free base |
| 14 | B5.b | ----NH(CH₂)---- | 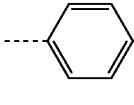 | ----H | •2.5HCl •0.5H₂O |
| 15 | B5.c | ----O(CH₂)---- | 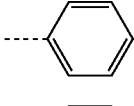 | ----H | free base |
| 16 | B2.a-2 | ----NH---- | 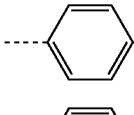 | ----H | •2.5HCl •0.5H₂O |
| 17 | B6.b | 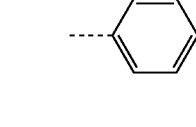 (E) | 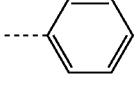 | 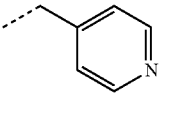 | trifluoroacetate |
| 18 | B6.b | 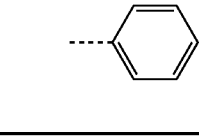 (E) | 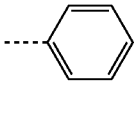 | 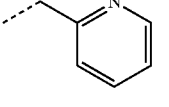 | free base |

C. Analytical Part

LCMS

General Procedure A

The HPLC measurement was performed using a Shimadzu 2010 LCMS-system comprising a pump, photo diode array detector (PDA) (wavelength used 220 nm), a column oven and a column as specified in the respective methods below. Flow from the column was split to a Shimadzu 2010 MSD detector. MS detector was configured with API-ES (atmospheric pressure electrospray ionization). Mass spectra were acquired by scanning from 100 to 1000. The interface voltage was 4500 V for positive ionization mode. The nebulizing gas flow was 1.5 l/min. The CDL (Curved Desolvation Line with heated capillary) temperature was 250° C. and the CDL voltage was 30 V. The heat block temperature was 200° C. The detector voltage was 1500 V.

General Procedure B

The LC measurement was performed using an Acquity Ultra Performance Liquid Chromatography (UPLC) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

LCMS Method 1

In addition to general procedure A: Reversed phase HPLC was carried out on a YMC-Pack ODS-AQ, 50×2.0 mm 7 μm column with a flow rate of 1.0 ml/min. Two mobile phases (mobile phase A: water with 0.1% TFA; mobile phase B: $CH_3CN$ with 0.05% TFA) were used to run a gradient from 99% A and 1% B to 90% A and 10% B in 0.01 min. Subsequently, a gradient was applied to 20% A and 80% B at 2.2 min. and this was hold for 0.28 min. Typical injection volumes of 1 μl were used. Oven temperature was 50° C. (MS polarity: positive)

LCMS Method 2

In addition to general procedure B: Reversed phase UPLC was carried out on a bridged ethylsiloxane/silica hybrid (BEH) C18 column (1.7 μm, 2.1×50 mm; Waters Acquity) with a flow rate of 0.8 ml/min. Two mobile phases (mobile phase A: 0.1% formic acid in $H_2O$/MeOH 95/5; mobile phase B: MeOH) were used to run a gradient condition from 95% A and 5% B to 5% A and 95% B in 1.3 min. and hold for 0.2 min. An injection volume of 0.5 μl was used. Cone voltage was 10 V for positive ionization mode and 20 V for negative ionization mode.

Melting Points

For a number of compounds, melting points were determined in open capillary tubes on a Mettler FP62 apparatus. Melting points were measured with a temperature gradient of 3 or 10° C./minute. Maximum temperature was 300° C. The melting point was read from a digital display.

TABLE 2

Retention time ($R_t$) in min., $MH^+$ (also $[M + H]^+$) peak (protonated molecule), LCMS method and m.p. (melting point in ° C.). 'n.d.' means not determined.

| Co. No. | $R_t$ | $MH^+$ | LCMS Method | m.p. (° C.) |
|---|---|---|---|---|
| 1 | 0.93 | 343 | 2 | 132.5 |
| 2 | 0.75 | 342 | 2 | n.d. |
| 3 | 0.94 | 323 | 2 | 133.8 |
| 4 | 0.85 | 337 | 2 | 289.5 |
| 5 | 0.82 | 339 | 2 | 199.7 |
| 6 | 0.83 | 373 | 2 | 180.3 |
| 7 | 0.96 | 353 | 2 | n.d. |
| 8 | 1.05 | 353 | 2 | 180.6 |
| 9 | 1.05 | 351 | 2 | 251.6 |
| 10 | 1.73 | 335 | 1 | n.d. |
| 11 | 1.03 | 349 | 2 | 135.8 |
| 12 | 0.85 | 337 | 2 | n.d. |
| 13 | 0.85 | 351 | 2 | 136.3 |
| 14 | 0.82 | 356 | 2 | n.d. |
| 15 | 0.99 | 357 | 2 | 142.1 |
| 16 | 0.75 | 342 | 2 | >300 |
| 17 | 1.14 | 426 | 2 | 163.9 |
| 18 | 1.20 | 426 | 2 | 121.4 |

D. Pharmacology

In vitro Binding Affinity for Human 5-$HT_6$ Receptor

Frozen membranes of human Serotonin 5-$HT_6$ receptor-transfected HEK cells were thawed, briefly homogenized using an Ultra-Turrax T25 homogeniser and diluted in 50 mM Tris-HCl assay buffer containing 10 mM $MgCl_2$, 1 mM EDTA and 10 μM Pargyline (adjusted to pH 7.4 with HCl) to an appropriate protein concentration optimized for specific and non-specific binding. Radioligand [$^3H$]Lysergic acid diethylamide (Perkin Elmer, specific activity ~80 Ci/mmol) was diluted in assay buffer at a concentration of 20 nM. Radioligand (20 μl), along with 40 μl of either the 10% DMSO control, Methiothepine ($10^{-5}$M final concentration for measurement of non specific binding), or compound of interest, was then incubated with 70 μl of the prepared membrane solution and 70 μl of WGA (wheat germ agglutinin) coated PVT (polyvinyltoluidene) beads (0.25 mg/well final concentration). The final concentration of radioligand per well was 2 nM. After shaking for 24 h. at RT, plates were counted in a Topcount™ scintillation counter. Percentage specific binding and competition binding curves were calculated using S-Plus software (Insightful).

TABLE 3 pIC50 Values (5-$HT_6$)

| Co. No. | pIC50 |
|---|---|
| 1 | 6.6 |
| 2 | 7.2 |
| 3 | 6.9 |
| 4 | 6.9 |
| 5 | 6.2 |
| 6 | 6.6 |
| 7 | 6.8 |
| 8 | 7.2 |
| 9 | 5.8 |
| 10 | n.d. |
| 11 | 6.4 |
| 12 | n.d. |
| 13 | 6.8 |
| 14 | 6.2 |
| 15 | 6.4 |
| 16 | n.d. |
| 17 | 5.9 |
| 18 | 5.2 |

In vitro Binding Assay for Human $H_3$ Receptor

Binding of compounds to the cloned human $H_3$ receptor, stably expressed in SK-N-MC cells, was performed as described earlier (Lovenberg T W, Pyati J, Chang H, Wilson S J, Erlander M G. Cloning of rat histamine $H_3$ receptor reveals distinct species pharmacological profiles. J Pharmacol Expt Ther 2000;293:771-778). Briefly, cell pellets from SK-N-MC cells expressing the human $H_3$ receptor were homogenized in 50 mM Tris-HCl/5 mM EDTA and recentrifuged at 30000 g for 30 min. Pellets were rehomogenized in 50 mM Tris/5 mM EDTA (pH 7.4). Membranes were incubated for 1 h at 25° C. with $^{125}$I-iodoproxyfan diluted with cold iodoproxifan in 50 mM Tris-HCl/5 mM EDTA. The final total iodoproxifan concentration in the reactions is 1 nM. The cold iodoproxifan is included at 0.975 nM and the $^{125}$I-iodoproxyfan is included at 0.025 nM final concentration. The reactions were terminated by filtration thru GF/B plates (pre-treated with 0.3% polyethylenimine) on the cell harvester. The plates were washed 5 times with buffer. Nonspecific binding was defined in the presence of 100 μM histamine Inhibitory concentration (responsible for 50% inhibition of maximal effect, $IC_{50}$) values were determined by a single site curve-fitting program (GraphPad, San Diego, Calif.) and converted to $K_i$ values based on a $^{125}$I-iodoproxyfan dissociation constant ($K_d$) of 1 nM.

TABLE 4

$K_i$ Values($H_3$)

| Co. No. | $K_i$ (nM) |
|---|---|
| 1 | 5000 |
| 2 | >10000 |
| 3 | >10000 |

TABLE 4-continued

| Co. No. | $K_i$ (nM) |
|---|---|
| 4 | >10000 |
| 5 | >10000 |
| 6 | >10000 |
| 7 | >10000 |
| 8 | >10000 |
| 9 | >10000 |
| 10 | n.d. |
| 11 | >10000 |
| 12 | n.d. |
| 13 | >10000 |
| 14 | >10000 |
| 15 | >10000 |
| 16 | >10000 |
| 17 | >10000 |
| 18 | >10000 |

E. COMPOSITION EXAMPLES

"Active ingredient" (A.I.) as used throughout these examples relates to a compound of Formula (I), the pharmaceutically acceptable acid or base addition salts thereof, and the stereoisomeric forms thereof Example E.1

Oral Drops

500 Grams of the A.I. was dissolved in 0.5 l of 2-hydroxypropanoic acid and 1.5 l of the polyethylene glycol at 60~80° C. After cooling to 30~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

Example E.2

Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example E.3

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose in 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

Example E.4

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

The invention claimed is:

1. A compound of formula (I)

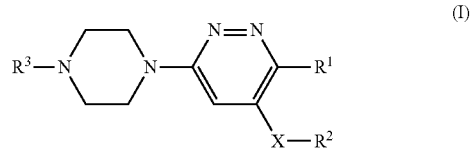

or a stereoisomeric form thereof, wherein
$R^1$ is chloro, trifluoromethyl or cyano;
$R^2$ is phenyl or phenyl substituted with halo;
$R^3$ is hydrogen, $C_{1-4}$-alkyl or pyridinylmethyl;
X is —O—, —NH—, —CH$_2$—, —CH(OH)—, —SO$_2$—, —CO—, —NH—CH$_2$—, —O—CH$_2$—, 1,2-ethenediyl or ethynediyl;
or a pharmaceutically acceptable addition salt thereof.

2. The compound according to claim 1 wherein
$R^1$ is trifluoromethyl;
$R^2$ is phenyl or phenyl substituted with fluoro;
$R^3$ is hydrogen, methyl or pyridinylmethyl;
X is —O—, —NH—, —CH$_2$—, —CH(OH)—, —SO$_2$—, —CO—, —NH—CH$_2$—, —O—CH$_2$—, 1,2-ethenediyl or ethynediyl;
or a pharmaceutically acceptable addition salt thereof.

3. The compound according to claim 1 wherein
$R^2$ is phenyl or phenyl substituted with one fluoro.

4. The compound according to claim 1 wherein the compound is N-(4-fluorophenyl)-6-(1-piperazinyl)-3-(trifluoromethyl)-4-pyridazinamine.

5. The compound N-(4-fluorophenyl)-6-(1-piperazinyl)-3-(trifluoromethyl)-4-pyridazinamine.2.5 HCl 0.5 H$_2$O.

6. A pharmaceutical composition comprising a pharmaceutically acceptable carrier and, as active ingredient, a therapeutically effective amount of a compound as defined in claim 1.

7. A pharmaceutical composition comprising a pharmaceutically acceptable carrier and, as active ingredient, a therapeutically effective amount of a compound as defined in claim 2.

8. A pharmaceutical composition comprising a pharmaceutically acceptable carrier and, as active ingredient, a therapeutically effective amount of a compound as defined in claim 3.

9. A pharmaceutical composition comprising a pharmaceutically acceptable carrier and, as active ingredient, a therapeutically effective amount of a compound as defined in claim 4.

10. A pharmaceutical composition comprising a pharmaceutically acceptable carrier and, as active ingredient, a therapeutically effective amount of a compound as defined claim 5.

* * * * *